(12) United States Patent
Sugimoto et al.

(10) Patent No.: US 8,318,991 B2
(45) Date of Patent: Nov. 27, 2012

(54) METHOD FOR PRODUCING HYDROGEN-CONTAINING FLUOROOLEFIN COMPOUND

(75) Inventors: Tatsuya Sugimoto, Tokyo (JP); Takefumi Suzuki, Tokyo (JP); Jo Konagawa, Tokyo (JP)

(73) Assignee: Zeon Corporation, Tokyo (JP)

( * ) Notice: Subject to any disclaimer, the term of this patent is extended or adjusted under 35 U.S.C. 154(b) by 23 days.

(21) Appl. No.: 12/990,858

(22) PCT Filed: Jul. 13, 2009

(86) PCT No.: PCT/JP2009/062686
§ 371 (c)(1),
(2), (4) Date: Nov. 3, 2010

(87) PCT Pub. No.: WO2010/007968
PCT Pub. Date: Jan. 21, 2010

(65) Prior Publication Data
US 2011/0060170 A1    Mar. 10, 2011

(30) Foreign Application Priority Data

Jul. 18, 2008   (JP) .................... 2008-187112
Sep. 17, 2008   (JP) .................... 2008-237416

(51) Int. Cl.
*C07C 21/00*   (2006.01)
*C07C 17/00*   (2006.01)
(52) U.S. Cl. ........................................ 570/153
(58) Field of Classification Search ............ None
See application file for complete search history.

(56) References Cited

U.S. PATENT DOCUMENTS

| | | | |
|---|---|---|---|
| 3,024,290 A | 3/1962 | Henne | |
| 3,567,788 A | 3/1971 | Carr et al. | |
| 4,814,522 A | 3/1989 | Weigert | |
| 5,045,634 A | 9/1991 | Fernandez et al. | |
| 5,171,902 A | 12/1992 | Krespan et al. | |
| 5,498,806 A | 3/1996 | Ichikawa et al. | |
| 5,756,869 A | 5/1998 | Yoshikawa et al. | |
| 6,166,276 A | 12/2000 | Sakyu et al. | |
| 6,395,700 B1 | 5/2002 | Yamada et al. | |

FOREIGN PATENT DOCUMENTS

| | | |
|---|---|---|
| EP | 0396974 A1 | 11/1990 |
| JP | 4-117333 A | 4/1992 |
| JP | 7-126197 A | 5/1995 |
| JP | 2000-86548 A | 3/2000 |
| JP | 2000-226346 A | 8/2000 |
| JP | 2000-247912 A | 9/2000 |
| JP | 2001-240569 A | 9/2001 |
| JP | 2002-293538 A | 10/2002 |
| WO | WO-99/33771 A1 | 7/1999 |

OTHER PUBLICATIONS

Fuller, G. et al. "Some Isomeric Hexafluorocyclobutanes and Pentafluorocyclobutenes" Journal of Chemical Society, 3198-3203 (1961).

Buxton, M.W. et al. "The Reactions of Highly Fluorinated Organic Compunds. Part V. 1H : 2H-*Hexafluorocyclobutane and* 1H-*Pentafluorocyclobut-1-ene*." Journal of Chemical Society, 1177-1179 (1954).

International Search Report for International Application No. PCT/JP2009/062686 (mailed Sep. 15, 2009).

*Primary Examiner* — Johann Richter
*Assistant Examiner* — Clinton Brooks
(74) *Attorney, Agent, or Firm* — Edwards Wildman Palmer LLP; David G. Conlin; Lisa Swiszez

(57) ABSTRACT

An unsaturated hydrogen-containing fluoroolefin compound is obtained by bringing an unsaturated fluorine-containing halogen compound into contact with 0.1 to 3 molar equivalents of hydrogen relative to the unsaturated fluorine-containing halogen compound in a vapor phase in the presence of a supported palladium catalyst in which an amount of supported palladium is 0.1% by weight to 2.5% by weight.

2 Claims, No Drawings

METHOD FOR PRODUCING HYDROGEN-CONTAINING FLUOROOLEFIN COMPOUND

CROSS-REFERENCE TO RELATED APPLICATIONS

This Application is a national phase application pursuant to 35 U.S.C. §371 of International Application No. PCT/JP2009/062686 filed Jul. 13, 2009, which claims the benefit of priority of Japanese Patent Application No. 2008-187112 filed Jul. 18, 2008, and Japanese Patent Application No. 2008/237416 filed Sep. 17, 2008. These applications are hereby incorporated herein by reference in their entireties.

TECHNICAL FIELD

The present invention relates to a method for producing a hydrogen-containing fluoroolefin compound which is useful as a raw material for: (i) a gas for a plasma reaction used for etching, CVD, or the like which is useful in a semiconductor device production field, (ii) a monomer from which a fluorine-containing polymer is made, (iii) an intermediate of a fluorine-containing medicine, or a hydrofluorocarbon solvent.

BACKGROUND ART

As for a hydrogen-containing fluoroolefin compound, a hydrogen-containing fluoroolefin compound having 4 to 6 carbon atoms is well known. Patent Literature 1 suggests a method for producing 1H,2H-hexafluorocyclopentene which is an unsaturated hydrogen-containing fluoroolefin compound having 4 to 6 carbon atoms. Specifically, a method is disclosed in which 1,2-dihalogenohexafluorocyclopentene, which serves as a starting material, is reduced by a hydrogen gas in the presence of a catalyst which consists mainly of copper, iron, chromium, or nickel, thereby obtaining 1H,2H-hexafluorocyclopentene as a main product.

On the other hand, as for a method for producing 1,1,2,2,3,3,4-heptafluorocyclopentane which is a saturated hydrogen-containing fluoroolefin compound, methods are suggested in each of which 1-chloroheptafluorocyclopentene, which serves as a starting material, is reduced by hydrogen gas in the presence of a supported catalyst containing at least palladium (see Patent Literatures 2 and 3).

Further, according to Non Patent Literature 1, hexafluorocyclobutene is treated with a metal hydride, thereby obtaining 1H-pentafluorocyclobutene.

According to Non Patent Literature 2, hexafluorocyclobutane, which can be obtained by causing lithium hydride aluminum hydrido to reduce dichlorohexafluorocyclobutane, is subjected to an alkali treatment, thereby obtaining 1H-pentafluorocyclobutene.

CITATION LIST

Patent Literature 1

Japanese Patent Application Publication, Tokukai, No. 2000-86548 A (Publication Date: Mar. 28, 2000)

Patent Literature 2

Japanese Patent Application Publication, Tokukai, No. 2000-226346 A (Publication Date: Aug. 15, 2000) (Specification of U.S. Pat. No. 6,166,276)

Patent Literature 3

Japanese Patent Application Publication, Tokukai, No. 2000-247912 A (Publication Date: Sep. 12, 2000)

Non Patent Literature 1

G. Fuller et al., Journal of Chemical Society, 3198 (1961)

Non Patent Literature 2

M. W. Buxton et al., Journal of Chemical Society, 1177 (1954)

SUMMARY OF INVENTION

Technical Problem

An object of the present invention is to provide a method which makes it possible to industrially produce, with excellent selectivity, a 1H-polyfluorocycloalkene compound which is an unsaturated hydrogen-containing fluoroolefin compound having 4 to 6 carbon atoms. Particularly in a reaction of the present invention, it is possible to produce, in a good yield, a 1H-polyfluorocycloalkene compound in the presence of a catalyst containing at least palladium, while preventing secondary production of an undesirable product by bringing a raw material into contact with hydrogen.

According to the method described in Patent Literature 1, for example, 1H, 2H-hexafluorocyclopentene is produced by use of a catalyst containing copper or nickel. However, there is a problem that the catalyst containing copper or nickel is less heat-resistant and the catalyst itself is therefore less durable and inappropriate for a long-term continuous reaction.

Each of Patent Literatures 2 and 3 is directed to substitute a hydrogen atom for a halogen atom by use of a catalyst containing palladium. According to Patent Literature 2, since a catalyst contains a large amount of metal, saturated heptafluorocyclopentane is obtained as a main product. According to Patent Literature 3, since a ratio of hydrogen to a raw material is too high though a catalyst contains a reduced amount of metal, saturated heptafluorocyclopentane is also obtained as a main product.

According to Non Patent Literature 1, hexafluorocyclobutene, which is used for a raw material and is a gaseous compound, is difficult to treat, and hexafluorocyclobutene needs to be cooled to an extremely low temperature while being dissolved in a solvent. In view of the circumstances, a method described in Non Patent Literature 1 is industrially inappropriate for mass production. According to Non Patent Literature 2, operation, in which hexafluorobutane is merely subjected to the alkali treatment, is also simple and easy. However, since there is little difference in boiling point between a raw material and pentafluorocyclobutene which is a target substance, it is extremely difficult to carry out purification. Therefore, this is less productive.

In order to attain the object, inventors of the present invention accomplished the present invention by finding that: an unsaturated fluorine-containing halogen compound is brought into contact with 0.1 to 3 molar equivalents of hydrogen relative to the unsaturated fluorine-containing halogen compound in a vapor phase in the presence of a supported palladium catalyst in which an amount of supported palladium is 0.1% by weight to 2.5% by weight, thereby producing an unsaturated hydrogen-containing fluoroolefin compound with excellent selectivity, especially while preventing secondary production of an undesired saturated product.

Further, since palladium is less abundant in the crust and is therefore expensive, the inventors carried out a further examination so as to cause an increase in productivity. As a result, the inventors found that: in a case where a weight ratio between palladium and bismuth which are used for a catalyst is optimized and the catalyst is subjected to a hydrogen reduction treatment at a temperature in a range of 200° C. to 350° C. while being prepared, it is possible to produce a hydrogen-containing fluoroolefin compound from an unsaturated fluorine-containing halogen compound with excellent selectivity and at a higher raw material conversion rate even by use of a catalyst which contains a reduced amount of supported palladium, while preventing generation of a saturated product.

Solution to Problem

Thus, according to the present invention, a method is provided for producing a hydrogen-containing fluoroolefin compound, including: bringing a fluorine-containing halogen compound into contact with 0.1 to 3 molar equivalents of hydrogen relative to the fluorine-containing halogen compound in a vapor phase in the presence of a supported palladium catalyst in which an amount of supported palladium is 0.1% by weight to 2.5% by weight;

said fluorine-containing halogen compound being represented by the formula (1):

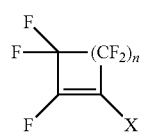

[Chem. 1]

wherein n represents an integer of 0 to 3, and X represents a chlorine atom, a bromine atom, or an iodine atom;

said hydrogen-containing fluoroolefin compound being represented by the formula (2):

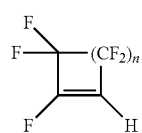

[Chem. 2]

wherein n represents an integer of 0 to 3.

Furthermore, it is preferable that the supported palladium catalyst be a catalyst in which a weight ratio between palladium and bismuth (Bi/Pd) falls within a range of 0.4 to 1.0 and which has been subjected to a hydrogen reduction treatment at a temperature in a range of 200° C. to 350° C.

Moreover, it is preferable that the fluorine-containing halogen compound be brought into contact with hydrogen in the vapor phase at a temperature of not less than 150° C.

The method of the present invention is suitably employed especially when the hydrogen-containing fluoroolefin compound represented by the formula (2) is 1H-pentafluorocyclobutene or 1H-heptafluorocyclopentene.

DESCRIPTION OF EMBODIMENTS

A production method of the present invention includes: bringing a fluorine-containing halogen compound into contact with 0.1 to 3 molar equivalents of hydrogen relative to the fluorine-containing halogen compound in a vapor phase in the presence of a supported palladium catalyst in which an amount of supported palladium is 0.1% by weight to 2.5% by weight; said fluorine-containing halogen compound being represented by the formula (1).

A fluorine-containing halogen compound used as a raw material is exemplified by a fluorine-containing cycloolefin compound in which X is a chlorine atom, a bromine atom, or an iodine atom as represented by the formula (1). Examples of the fluorine-containing cycloolefin compound encompass: fluorine-containing cycloolefin compounds having 3 carbon atoms such as 1-chlorotrifluorocyclopropene, 1-bromotrifluorocyclopropene, and 1-iodinetrifluorocyclopropene; fluorine-containing cycloolefin compounds having 4 carbon atoms such as 1-chloropentafluorocyclobutene, 1-bromopentafluorocyclobutene, and 1-iodinepentafluorocyclobutene; fluorine-containing cycloolefin compounds having 5 carbon atoms such as 1-chloroheptafluorocyclopentene, 1-bromoheptafluorocyclopentene, and 1-iodineheptafluorocyclopentene; and fluorine-containing cycloolefin compounds having 6 carbon atoms such as 1-chlorononafluorocyclohexene, 1-bromononafluorocyclohexene, and 1-iodinenonafluorocyclohexene. Among these fluorine-containing cycloolefin compounds, the fluorine-containing cycloolefin compounds having 4 carbon atoms such as 1-chloropentafluorocyclobutene, 1-bromopentafluorocyclobutene, and 1-iodinepentafluorocyclobutene and the fluorine-containing cycloolefin compounds having 5 carbon atoms such as 1-chloroheptafluorocyclopentene, 1-bromoheptafluorocyclopentene, and 1-iodineheptafluorocyclopentene are more preferable.

It is possible to produce a fluorine-containing halogen compound used as a raw material in accordance with the methods described in U.S. Pat. No. 3,024,290, U.S. Pat. No. 3,567,788, USSR Patent No. 383367, and others. According to these methods, 1,2-dihalogenotetrafluorocyclobutene, 1,2-dihalogenohexafluorocyclopentene, or the like, which serves as a starting material, is brought into contact with a metal fluoride such as potassium fluoride or cesium fluoride, thereby producing a fluorine-containing halogen compound. Alternatively, according to a method described in U.S. Pat. No. 4,814,522, it is also possible to produce perfluorocycloolefin and a chlorofluoroalkene in the presence of a catalyst through a chlorine-fluorine halogen exchange.

A hydrogen-containing fluoroolefin compound obtained in accordance with the present invention is a compound in which the olefin part has hydrogen, as represented by the formula (2). Specific examples of the hydrogen-containing fluoroolefin compound encompass: 1H-trifluorocyclopropene, 1H-pentafluorocyclobutene, 1H-heptafluorocyclopentene, and 1H-nonafluorocyclohexene. Among these hydrogen-containing fluoroolefin compounds, 1H-pentafluorocyclobutene and 1H-heptafluorocyclopentene are more preferable.

A catalyst used in the present invention for a hydrogenation reaction contains at least palladium. Palladium is used while being supported by a support. Preferable examples of the support encompass: activated carbon, alumina, silica, zirconia, titania, and these materials whose surfaces have been subjected to a surface treatment such as fluorination, In particular, activated carbon and alumina are preferable due to their good hydrogenation efficiency.

In a reaction pattern of the present invention, it is preferable that the support be granular since it is brought into contact with a hydrogen gas in a vapor phase. Though an average particle size of the support hardly affects a reaction, for example, a support having an average particle size of 0.1 mm to 10 mm, and more preferably of 2 mm to 5 mm is suitably employed from the viewpoint of securement of fluidity of the support in the vapor phase.

Examples of the activated carbon used for the support encompass: vegetable activated carbons made of: wood, charcoal, carbon from a coconut shell, carbon from a coconut stone, brasque, and the like; coal activated carbons made of: peat, lignite, brown coal, bituminous coal, anthracite, and the like; petroleum-residue activated carbons; petroleum activated carbons made of: sulfate sludge, oil carbon, and the like; and an activated carbon made of a synthetic resin. Since various kinds of activated carbon are commercially available, it is only necessary to select an activated carbon from these kinds and use it.

Alumina is not particularly limited, either. Generally, alumina is obtained by molding and dehydrating a precipitate produced from an aluminum salt aqueous solution by use of a basic substance such as ammonia. Normally, it is possible to preferably employ γ-alumina which is commercially available for catalyst supporting or for drying.

An amount of supported palladium is 0.1% by weight to 2.5% by weight, and preferably 0.2% by weight to 2% by weight. A larger amount of supported palladium causes too high catalyst activity. This tends to induce a hydrogenation reaction of a carbon-carbon double bond in addition to a hydrogenolysis of a carbon-halogen (except fluorine) bond, thereby secondarily producing an undesirable product. In contrast, a smaller amount of supported palladium, which decreases an efficiency of a hydrogenation reaction, is unfavorable.

In order to modulate catalyst activity, it is possible to use the palladium catalyst with which a metal serving as a second component is alloyed. The metal serving as the second component is selected from silver, copper, gold, zinc, tellurium, subchloride, chromium, molybdenum, thallium, tin, bismuth, lead, ruthenium, platinum, rhodium, and the like. These metals can be added in combination of two or more kinds. Such a metal component is added in, for example, 0.01 part by weight to 500 parts by weight, preferably 0.1 part by weight to 300 parts by weight, and more preferably 0.1 part by weight to 50 parts by weight, with respect to 100 parts by weight of palladium.

For example, a hydrogenation catalyst as mentioned above is prepared as follows: An aqueous solution of metal salts such as palladium nitrate and palladium chloride is mixed with an aqueous solution of an added metal salt in a desired ratio and at a desired concentration. Thereafter, a support is impregnated with the mixed aqueous solution. Subsequently, the impregnated support is dried and then treated at a high temperature of, for example, 100° C. to 600° C. In this case, it is also possible to carry out the preparation while supplying a reducing substance such as hydrogen according to need.

According to the production method of the present invention in which production method the compound represented by the formula (2) is produced by bringing the fluorine-containing halogen compound represented by the formula (1) into contact with hydrogen, it is preferable that the supported palladium catalyst be a catalyst in which a weight ratio between palladium and bismuth (Bi/Pd) falls within a range of 0.4 to 1.0 and which has been subjected to a hydrogen reduction treatment at a temperature in a range of 200° C. to 350° C.

In a case where the supported palladium catalyst contains palladium and bismuth, it is preferable to use palladium and bismuth which are supported by a support while being alloyed. Preferable examples of the support encompass: activated carbon, alumina, silica, zirconia, titania, and these materials whose surfaces have been subjected to a surface treatment such as fluorination. In particular, activated carbon and alumina are preferable due to their good hydrogenation efficiency.

In the case where the supported palladium catalyst contains palladium and bismuth, an amount of supported palladium is generally 0.1% by weight to 2.5% by weight, and preferably 0.2% by weight to 2% by weight. A larger amount of supported palladium causes too high catalyst activity. This tends to induce a hydrogenation reaction of a carbon-carbon double bond in addition to a hydrogenolysis of a carbon-halogen (except fluorine) bond, thereby secondarily producing an undesirable product. In contrast, a smaller amount of supported palladium, which decreases an efficiency of a hydrogenation reaction, is unfavorable.

In the case where the supported palladium catalyst contains palladium and bismuth, the supported palladium catalyst is prepared so that bismuth is used in a weight ratio Bi/Pd of 0.4 to 1.0, and preferably 0.4 to 0.8, with respect to palladium. As long as bismuth is used in this range, it is possible to easily and favorably modulate activity of the supported palladium catalyst.

For example, the hydrogenation catalyst, i.e., the supported palladium catalyst containing palladium and bismuth is prepared as follows: An aqueous solution of a metal salt such as palladium nitrate or palladium chloride is mixed with an aqueous solution of a bismuth salt such as bismuth nitrate in a desired ratio and at a desired concentration. Thereafter, a support is impregnated with a mixed aqueous solution and then dried. Further, the preparation is carried out at a temperature in a range of, for example, 200° C. to 350° C., preferably 250° C. to 350° C., and more preferably 250° C. to 300° C. while hydrogen is being supplied. In this case, it is possible to (i) prevent hydrogenation of olefin and (ii) enhance selectivity by setting the temperature at which the support is brought into contact with hydrogen to not less than 200° C. In contrast, it is possible to (i) prevent sintering of a palladium metal, (ii) obtain a catalyst having favorable activity, and (iii) enhance a raw material conversion rate by setting the temperature to not more than 350° C. In a case where a hydrogen reduction treatment is carried out at the temperature in the above range, palladium seems to be alloyed with bismuth while being homogeneously dispersed in the support. Therefore, it is possible to produce a target substance with excellent selectivity while maintaining a high raw material conversion rate.

For a pattern of a hydrogenation reaction of the present invention, a batch reaction or a vapor phase flow reaction in which raw materials are continuously supplied to a reactor and then reaction products are continuously extracted from the reactor. Since hydrogen halide is generated during the hydrogenation reaction of the present invention, the vapor phase flow reaction is suitable from the viewpoint of prevention of corrosion in the reactor. A reactor for use in the hydrogenation reaction is not particularly limited. Generally, a pressure vessel is used in the case of the batch reaction and a reactor including at least two reactors which are connected in series (e.g. a cascade reactor) is used in the case of the vapor phase flow reaction.

A temperature at which a fluorine-containing halogen compound is brought into contact with hydrogen in a vapor phase, i.e., a minimum temperature at which a hydrogenation reaction is carried out is a temperature at which a reacting raw material generally vapors, i.e., preferably 150° C., and more preferably 200° C. A maximum temperature at which the hydrogenation reaction is carried out is, for example, 450° C., and more preferably 300° C. Time during which a raw material and hydrogen contact with each other is, for example, 0.1 second to 300 seconds, and particularly 0.5 second to 30 seconds in the case of the vapor phase flow reaction, and 0.1 hour to 15 hours, and preferably 1 hour to 10 hours in the case of the batch reaction.

An amount of hydrogen with which a fluorine-containing halogen compound serving as a raw material is brought into contact is 0.1 to 3 molar equivalents, preferably 1 to 3 molar equivalents, and more preferably 1.5 to 3 molar equivalents, relative to the raw material. A larger amount of hydrogen tends to induce a hydrogenation reaction of a carbon-carbon double bond in addition to a hydrogenolysis of a carbon-halogen (except fluorine) bond, thereby secondarily producing an undesirable product. In contrast, a smaller amount of hydrogen, which decreases an efficiency of a hydrogenation reaction, is unfavorable. In other words, in a case where an amount of hydrogen is not less than 0.1 molar equivalent and not more than 3 molar equivalents, it is possible to prevent secondary production of an undesirable product and further to increase an efficiency of a hydrogenation reaction.

During a hydrogenation reaction, it is possible to mix an inactive gas as a diluent so as to prevent heat generation. A diluent gas can be appropriately selected from nitrogen, a rare gas, perfluorocarbon, and hydrofluorocarbon.

According to the reaction of the present invention, it is possible to remove hydrogen halide such as hydrogen chloride generated in response to a hydrogenolysis of a carbon-halogen bond by bringing hydrogen halide, together with a reaction product, into contact with water.

EXAMPLES

The present invention is more specifically described below with reference to Examples, which do not limit the scope of the present invention. Note that "part(s)" and "%" refer to "part(s) by weight" and "% by weight", respectively unless otherwise specified.

Analytical conditions employed in Examples are as below.
Gas Chromatography Analysis (GC Analysis)
Apparatus: Gas chromatography mass spectrometer "HP6890" (produced by Agilent Technologies)
Column: Inert Capl (Registered Trademark) (produced by GL Sciences Inc.; length: 60 m, caliber: 250 μm, thickness: 1.50 μm)
Injection temperature: 150° C.
Detector temperature: 250° C.
Carrier gas: Nitrogen (53.0 mL/min)
Makeup gas: Nitrogen (30 mL/min), Hydrogen (50 mL/min), Atmosphere (400 mL/min)
Split ratio: 100/1
Temperature rising program: Temperature (1) is retained at 40° C. for 20 minutes, (2) rises at a rate of 40° C./min, and (3) is retained at 250° C. for 5.25 minutes.
Detector: FID Catalyst Preparation Example 1

One hundred parts of activated carbon (produced by Takeda Pharmaceutical Company Limited, product name: SHIRASAGI G2X-4/6) was weighed and placed in an eggplant-shaped flask, to which approximately 150 parts of an approximately 20% nitric aqueous solution were added. Then, a resulting solution was left for a night. Separately, 0.928 part of a bismuth nitrate (III) pentahydrate and 200 parts of an approximately 30% nitric aqueous solution were mixed in a beaker. Then, a resulting bismuth nitrate aqueous solution was completely dissolved in a hot-water bath. Besides, 3.33 parts of palladium chloride (II) was dissolved in 50 parts of 24% hydrochloric acid, so that a palladium chloride hydrochloric acid aqueous solution was prepared. The bismuth nitrate aqueous solution and the palladium chloride hydrochloric acid solution which had been prepared as described above were mixed. Thereafter, a mixed solution was poured into the above flask in which the activated carbon was contained. Then, the mixed solution was settled at room temperature for 2 days.

A metal-impregnated activated carbon settled for 2 days was subjected to separation by filtration. Then, a bath temperature was raised to 150° C., thereby causing a rotary evaporator to dry the metal-impregnated activated carbon by decompression. Subsequently, a reaction vessel (1 inch×300 mm) was filled with the metal-impregnated activated carbon thus dried. Then, the bath temperature was raised from 150° C. to 300° C. in increments of 50° C. while nitrogen was being flowed into the reaction vessel at a flow rate of 200 ml/min, so that the metal-impregnated activated carbon was sintered. After the sintering was carried out at 300° C. for 1 hour, nitrogen was replaced with hydrogen. Then, a reduction was carried out while hydrogen was being flowed into the reaction vessel at a flow rate of 300 ml/min, so that a catalyst was prepared. Respective amounts of supported palladium and supported bismuth were 2% and 0.2% of a weight of the activated carbon.

Catalyst Preparation Example 2

As in Preparation Example 1, a catalyst was prepared in which respective amounts of supported palladium and supported bismuth were 4.5% and 0.5% of a weight of activated carbon.

Example 1

A reaction vessel (⅜ inch×20 cm, produced by SUS316) was filled with 0.25 g of a supported palladium catalyst (2% Pd/C, produced by N.E. CHEMCAT CORPORATION), as a hydrogenation catalyst, in which an amount of supported palladium was 2% and whose support was carbon. A temperature of the reaction vessel was raised to 200° C. while nitrogen was being introduced into the reaction vessel for 30 minutes at a flow rate of 100 ml/min, and hydrogen was then being introduced into the reaction vessel at a flow rate of 200 ml/min. When the temperature of the reaction vessel reached a preset temperature, hydrogen was set to be introduced at a flow rate of 49 ml/min (an amount of hydrogen relative to a raw material=2 molar equivalents). Then, 1-chloroheptafluorocyclopentene which was a raw material was supplied by use of a pump at a rate of 13 g/h while being vaporized from an upper part of the reaction vessel, so that the reaction was carried out for 8 hours. A gas released from the reaction vessel was bubbled in water, thereby removing by-product hydrogen chloride. Subsequently, the gas was trapped in a glass trap soaked in an ethanol/dry ice bath. As a result of a gas-chromatographic analysis of contents of a product, the product was composed of 49.8% of 1,3,3,4,4,5,5-heptafluorocyclopentene (boiling point: 46° C.; "7F-CPE" in Table 1) which was a target substance, 31.6% of 1-chloroheptafluorocyclopentene (boiling point: 56° C.) which was a raw material, 18.0% of 1,1,2,2,3,3,4-heptafluorocyclopentane (boiling point: 82° C.; "7F-CPA" in Table 1) which was a by-product, 0.1% of 1,3,3,4,4,5,5-hexafluorocyclopentene (boiling point: 74° C.; "6F-CPE" in Table 1), 0% of 1,1,2,2,3,3-hexafluorocyclopentane (boiling point: 88° C.; "6F-CPA" in Table 1), and 0.5% of the other compound. Note, in the present example, that yields (%) of the respective products are area percents of respective peaks which area percents are found based on peak areas measured in gas chromatography. A result of the gas-chromatographic analysis is shown in Table 1.

Examples 2 Through 6, Comparative Examples 1 Through 3

Reactions were caused so as to carry out analyses as in the case of Example 1, except that kinds and amounts of catalysts, amounts of hydrogen, and reaction temperatures were changed as shown in Table 1. Results of the analyses are shown in Table 1.

TABLE 1

|  |  | Examples | | | | | | Comparative Examples | | |
|---|---|---|---|---|---|---|---|---|---|---|
|  |  | 1 | 2 | 3 | 4 | 5 | 6 | 1 | 2 | 3 |
| Catalyst kind* | | (A) | (B) | (B) | (B) | (B) | (C) | (D) | (E) | (F) |
| Catalyst amount (g) | | 0.25 | 0.5 | 0.5 | 0.5 | 1.0 | 0.25 | 1.0 | 0.25 | 0.25 |
| Hydrogen amount (mol) | | 2 | 2 | 2 | 1 | 1 | 2 | 3 | 2 | 2 |
| Reaction temperature (° C.) | | 200 | 200 | 250 | 200 | 200 | 200 | 150 | 200 | 200 |
| Product | Raw material | 31.6 | 16.9 | 19.1 | 50.8 | 29.7 | 30.1 | 0.1 | 99.1 | 18.9 |
| Composition** | 7F-CPE | 49.8 | 65.1 | 67.3 | 44.8 | 62.4 | 55.7 | 16.3 | 0.3 | 37.8 |
| | 7F-CPA | 18.0 | 14.0 | 10.2 | 2.2 | 3.5 | 12.0 | 83.4 | 0.1 | 40.6 |
| | 6F-CPE | 0.1 | 2.7 | 1.1 | 0.3 | 1.1 | 1.6 | 0.1 | 0.1 | 0.1 |
| | 6F-CPA | 0.0 | 0.9 | 1.7 | 1.1 | 1.7 | 0.4 | 0.0 | 0.1 | 0.1 |
| | Other | 0.5 | 0.4 | 0.6 | 0.8 | 1.6 | 0.2 | 0.1 | 0.3 | 0.5 |

*Catalyst kind:
(A) 2% Pd/C, produced by N.E. CHEMCAT CORPORATION
(B) 1% Pd/C, produced by N.E. CHEMCAT CORPORATION
(C) 2% Pd-0.2% Bi/C, obtained in Catalyst Preparation Example 1
(D) 4.5% Pd/C-0.5% Bi/C, obtained in Catalyst Preparation Example 2
(E) 2% Ru/C, produced by N.E. CHEMCAT CORPORATION
(F) 3% Pd/C, produced by N.E. CHEMCAT CORPORATION
**Unit of Product Composition: Peak area % measured in gas chromatography These results show that 1,3,3,4,4,5,5-heptafluorocyclopentene which is a target substance is selectively obtained. Note that it is possible to separate a product, by precision distillation, into 1,3,3,4,4,5,5-heptafluorocyclopentene which is a target substance, a raw material, and a by-product.

Example 7

A reaction vessel (3/8 inch×20 cm, produced by SUS316) was filled with 0.5 g of a palladium-bismuth-alloy catalyst, as a hydrogenation catalyst, which had been prepared in Catalyst Preparation Example 1A temperature of the reaction vessel was raised to 200° C. while nitrogen was being introduced into the reaction vessel for 30 minutes at a flow rate of 100 ml/min, and hydrogen was then being introduced into the reaction vessel at a flow rate of 200 ml/min. When the temperature of the reaction vessel reached a preset temperature, hydrogen was set to be introduced at a flow rate of 49 ml/min (2 molar equivalents). Then, 1-chloropentafluorocyclobutene which was a raw material was supplied by use of a pump at a rate of 10 g/h while being vaporized from an upper part of the reaction vessel, so that the reaction was carried out for 8 hours. A gas released from the reaction vessel was bubbled in water, thereby removing by-product hydrogen chloride. Subsequently, the gas was trapped in a glass trap soaked in an ethanol/dry ice bath. As a result of a gas-chromatographic analysis of contents of a product, the product was composed of 54.8% of 1,3,3,4,4-pentafluorocyclobutene (boiling point: 26° C.) which was a target substance, 26.4% of 1-chloropentafluorocyclobutene (boiling point: 33° C.) which was a raw material, 17.8% of 1,1,2,2,3-pentafluorocyclobutane (boiling point: 51° C.) which was a by-product, and 0.8% of 3,3,4,4-tetrafluorocyclobutene (boiling point: 50° C.).

[Preparation of Catalyst 8]

One hundred parts of activated carbon (produced by Takeda Pharmaceutical Company Limited, product name: SHIRASAGI G2X-4/6) was weighed and placed in an eggplant-shaped flask, to which approximately 150 parts of an approximately 20% nitric aqueous solution were added. Then, a resulting solution was left for a night. Separately, 1.856 part of a bismuth nitrate (III) pentahydrate and 200 parts of an approximately 30% nitric aqueous solution were mixed in a beaker. Then, a resulting bismuth nitrate aqueous solution was completely dissolved in a hot-water bath.

Besides, 0.83 part of palladium chloride (II) was dissolved in 50 parts of 24% hydrochloric acid, so that a palladium chloride hydrochloric acid aqueous solution was prepared. The bismuth nitrate aqueous solution and the palladium chloride hydrochloric acid solution which had been prepared as described above were mixed. Thereafter, a mixed solution was poured into the above flask in which the activated carbon was contained. Then, the mixed solution was settled at room temperature for 2 days.

A metal-impregnated activated carbon settled for 2 days was subjected to separation by filtration. Then, a bath temperature was raised to 150° C., thereby causing a rotary evaporator to dry the metal-impregnated activated carbon by decompression. Subsequently, a reaction vessel (1 inch×300 mm) was filled with the metal-impregnated activated carbon thus dried. Then, the bath temperature was raised from 150° C. to 300° C. in increments of 50° C. while nitrogen was being flowed into the reaction vessel at a flow rate of 200 ml/min, so that the metal-impregnated activated carbon was sintered. After the sintering was carried out at 300° C. for 1 hour, nitrogen was replaced with hydrogen. Then, a reduction was carried out while hydrogen was being flowed into the reaction vessel at a flow rate of 300 ml/min, so that a catalyst was prepared. Respective amounts of supported palladium and supported bismuth were 0.5% and 0.4% of a weight of the activated carbon.

[Preparation of Catalysts 9, 10, and 11]

Catalysts in each of which respective weight ratios of palladium and bismuth to activated carbon are as shown in Table 2 were prepared as in the case of the preparation of the catalyst 8, except that respective amounts of the bismuth nitrate pentahydrate and the palladium chloride were adjusted.

TABLE 2

|            | Pd (%) | Bi (%) |
|------------|--------|--------|
| Catalyst 8  | 0.5    | 0.4    |
| Catalyst 9  | 1.0    | 0.8    |
| Catalyst 10 | 1.0    | 0.4    |
| Catalyst 11 | 4.5    | 0.5    |

[Preparation of Catalyst 12]

A catalyst 12 was prepared as in the case of the preparation of the catalyst 8, except that, after metal-impregnated activated carbon was sintered at 300° C. for 1 hour, a temperature of a reaction vessel was decreased to 250° C. and then nitrogen was replaced with hydrogen. Respective amounts of supported palladium and supported bismuth were 0.5% and 0.4% of a weight of the activated carbon.

[Preparation of Catalyst 13]

A catalyst 13 was prepared as in the case of the preparation of the catalyst 12, except that a temperature at which a raw material was brought into contact with hydrogen was set to 150° C. Respective amounts of supported palladium and supported bismuth were 0.5% and 0.4% of a weight of activated carbon.

[Preparation of Catalyst 14]

A catalyst 14 was prepared as in the case of the preparation of the catalyst 8, except that, after metal-impregnated activated carbon was sintered at 300° C. for 1 hour, a temperature of a reaction vessel was raised to 450° C. and then nitrogen was replaced with hydrogen. Respective amounts of supported palladium and supported bismuth were 0.5% and 0.4% of a weight of the activated carbon.

Example 8

A reaction vessel (3/8 inch×20 cm, produced by SUS316) was filled with 3 g of Catalyst 8 as a hydrogenation catalyst. A temperature of the reaction vessel was raised to 200° C. while nitrogen was being introduced into the reaction vessel for 30 minutes at a flow rate of 100 ml/min, and hydrogen was then being introduced into the reaction vessel at a flow rate of 200 ml/min. When the temperature of the reaction vessel reached a preset temperature, hydrogen was set to be introduced at a flow rate of 63 ml/min (an amount of hydrogen relative to a raw material=2.5 molar equivalents). Then, 1-chloroheptafluorocyclopentene which was a raw material was supplied by use of a pump at a rate of 13 g/h while being vaporized from an upper part of the reaction vessel, so that the reaction was carried out for 8 hours. A gas released from the reaction vessel was bubbled in water, thereby removing by-product hydrogen chloride. Subsequently, the gas was trapped in a glass trap soaked in an ethanol/dry ice bath. As a result of a gas-chromatographic analysis of contents of a product, the product was composed of 68.74% of 1,3,3,4,4,5,5-heptafluorocyclopentene (boiling point: 46° C.; "7F-CPE" in Table 3) which was a target substance, 10.12% of 1-chloroheptafluorocyclopentene (boiling point: 56° C.) which was a raw material, 7.46% of 1,1,2,2,3,3,4-heptafluorocyclopentane (boiling point: 82° C.; "7F-CPA" in Table 3) which was a by-product, 5.91% of 1,3,3,4,4,5,5-hexafluorocyclopentene (boiling point: 74° C.; "6F-CPE" in Table 3), 5.0% of 1,1,2,2,3,3-hexafluorocyclopentane (boiling point: 88° C.; "6F-CPA" in Table 3), and 2.77% of the other compound. Note, in the present example, that yields (%) of the respective products are area percents of respective peaks which area percents are found based on peak areas measured in gas chromatography. A result of the gas-chromatographic analysis is shown in Table 3.

Examples 9 Through 11, Comparative Examples 4 Through 6

Reactions were caused so as to carry out analyses as in the case of Example 8, except that kinds and amounts of catalysts, amounts of hydrogen, and reaction temperatures were changed as shown in Table 3. Results of the analyses are shown in Table 3.

TABLE 3

|  |  | Examples | | | | Comparative Examples | | |
|---|---|---|---|---|---|---|---|---|
|  |  | 8 | 9 | 10 | 11 | 4 | 5 | 6 |
| Catalyst | Number | 8 | 9 | 10 | 12 | 11 | 13 | 14 |
|  | Bi/Pd ratio | 0.8 | 0.8 | 0.4 | 0.8 | 0.11 | 0.8 | 0.8 |
|  | Reduction temperature (° C.) | 300 | 300 | 300 | 250 | 300 | 150 | 450 |
|  | Amount (g) | 3.0 | 3.0 | 1.0 | 3.0 | 0.25 | 3.0 | 3.0 |
|  | Raw material (g/h) | 13 | 13 | 13 | 13 | 13 | 13 | 13 |
| Hydrogen | Amount (Pa·m$^3$/s) | $1.0647 \times 10^{-1}$ | $1.0647 \times 10^{-1}$ | $4.225 \times 10^{-2}$ | $1.0647 \times 10^{-1}$ | $1.0647 \times 10^{-1}$ | $2.1125 \times 10^{-1}$ | $2.1125 \times 10^{-1}$ |
|  | Amount (mol) | 2.5 | 2.5 | 1 | 2.8 | 2.5 | 5 | 5 |
|  | Reaction time (hr) | 8 | 8 | 8 | 8 | 8 | 8 | 8 |
|  | Reaction temperature (° C.) | 200 | 200 | 200 | 200 | 200 | 200 | 200 |
| Composition* | Raw material | 10.12 | 6.14 | 10.50 | 12.25 | 28.2 | 6.24 | 69.04 |
|  | 7F-CPE | 68.74 | 75.28 | 67.12 | 66.68 | 39.6 | 34.37 | 24.18 |
|  | 6F-CPE | 5.91 | 4.05 | 1.36 | 5.23 | 0.29 | 4.02 | 0.31 |
|  | 7F-CPA | 7.46 | 8.34 | 16.97 | 8.10 | 32.18 | 50.72 | 3.16 |
|  | 6F-CPA | 5.00 | 4.45 | 2.60 | 5.23 | 0.2 | 3.68 | 3.15 |
|  | Other | 2.77 | 1.74 | 1.45 | 2.51 | 0.07 | 0.97 | 0.16 |

*Unit of Product Composition: Peak area % measured in gas chromatography

These results show that a target substance is selectively obtained in accordance with the present invention. Note that it is possible to separate a product, by precision distillation, into a target substance, a raw material, and a by-product.

On the other hand, these results show that, in a case where a weight ratio between palladium and bismuth (Bi/Pd) is beyond a range of 0.4 to 1.0 and an amount of supported palladium is too large, a reduction reaction of a fluorine-containing halogen compound represented by the formula (1)

tends to progress and an alkyl compound is therefore comparatively easily produced (see Comparative Example 4).

These results also show that, in a case where the weight ratio between palladium and bismuth (Bi/Pd) falls within the range of 0.4 to 1.0 but a catalyst is reduced at a too low temperature, an alkyl compound is easily produced (see Comparative Example 5). In contrast, it seems that, in a case where a catalyst is reduced at a too high temperature, a palladium metal is sintered, thereby blocking pores on activated carbon and causing a reduction in effective surface area. This brought about a reduction in raw material conversion rate (see Comparative Example 6).

INDUSTRIAL APPLICABILITY

A production method according to the present invention is applicable to a semiconductor device production field.

The invention claimed is:

1. A method for producing a hydrogen-containing fluoroolefin compound, comprising:
   bringing a fluorine-containing halogen compound into contact with 0.1 to 3 molar equivalents of hydrogen relative to the fluorine-containing halogen compound in a vapor phase in the presence of a supported palladium catalyst in which an amount of supported palladium is 0.1% by weight to 2.5% by weight;
   wherein the supported palladium catalyst is a catalyst in which a weight ratio between palladium and bismuth (Bi/Pd) falls within a range of 0.4 to 0.8 and which has been prepared by subjection to a hydrogen reduction treatment at a temperature in a range of 250° C. to 350° C.;
   said fluorine-containing halogen compound being represented by the formula (1):

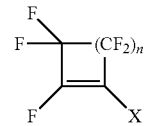

wherein n is 2, and X represents a chlorine atom, a bromine atom, or an iodine atom;

said hydrogen-containing fluoroolefin compound being represented by the formula (2):

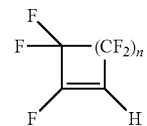

wherein n is 2.

2. The method as set forth in claim 1, wherein the fluorine-containing halogen compound is brought into contact with hydrogen in the vapor phase at a temperature of not less than 150° C.

* * * * *